United States Patent

Previdoli et al.

[11] Patent Number: 4,545,934
[45] Date of Patent: Oct. 8, 1985

[54] PROCESS FOR THE PRODUCTON OF 4-SUBSTITUTED ACETOACETIC ACID DERIVATIVES

[75] Inventors: Felix Previdoli, Ried bei Brig; Leander Tenud, Visp, both of Switzerland

[73] Assignee: Lonza Ltd., Basel, Switzerland

[21] Appl. No.: 591,926

[22] Filed: Mar. 21, 1984

[30] Foreign Application Priority Data

May 26, 1983 [CH] Switzerland ............... 2878/83

[51] Int. Cl.$^4$ ............................................. C07C 45/00
[52] U.S. Cl. ............................. 260/239 E; 560/175; 560/54
[58] Field of Search ............. 560/174, 54; 260/239 E

[56] References Cited

FOREIGN PATENT DOCUMENTS 31608 3/1974 Japan .

*Primary Examiner*—John Kight
*Assistant Examiner*—Marvin L. Moore
*Attorney, Agent, or Firm*—Fisher, Christen & Sabol

[57] ABSTRACT

Process for the production of 4-substituted acetoacetic acid derivatives. An acetoacetic acid derivative having the formula:

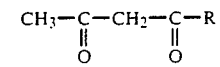

wherein R is alkoxy having 1 to 6 C atoms, phenoxy, $-NR'_2$, wherein R' is alkyl having 1 to 6 C atoms or aryl, or $NR'_2$, which is azetidine, pyrrolidine or piperidine, is treated with a secondary amine at an elevated temperature and in the presence of an organic solvent. The water formed is separated. The intermediate is converted into the corresponding 3-enamine carboxylic acid derivative. The derivative is converted by treatment with sodium amide in liquid ammonia into the corresponding sodium salt. The sodium salt is converted by treatment with a halogen compound having the formula $R_1CH_2X$ or $R_1R_2CHX$, wherein $R_1$ and $R_2$ each are alkyl, alkenyl, alkinyl or aryl and X is chlorine, bromine or iodide, into the corresponding 4-substituted enamino derivative. The derivative is hydrolyzed into the 4-substituted acetoacetic acid derivative.

12 Claims, No Drawings

PROCESS FOR THE PRODUCTON OF 4-SUBSTITUTED ACETOACETIC ACID DERIVATIVES

BACKGROUND OF THE INVENTION

1. Field of the Invention

The invention relates to a process for the production of 4-substituted acetoacetic acid derivatives from the corresponding acetoacetic acid derivatives.

2. Prior Art

It is known that in the case of the alkylation of acetoacetic esters, the alkylation takes place on the second carbon atom. Whenever the alkylation, however, is to take place on the fourth carbon atom, either the so-called dianion (discarbanion) of the acetoacetic ester must be formed. [*J. Org. Chem.*, 29, (1964), p. 3249; *J. Am. Chem. Sec.*, 92, (1970), p. 6702; *J. Am. Chem. Soc.*, 96, (1974), p. 1032], or else one must start out from the lithium salt of the corresponding 3-pyrrolidone derivative of the acetoacetic acid ester [Japanese Patent Publication No. 31,608 (1974)].

Whenever the dianion is formed with the aid of potassium amide in liquid ammonia, poor yields of dianion are obtained and thus also poor yields (less than 37 percent) of the desired 4-substituted product are obtained [*J. Org. Chem.*, 29, (1964), p. 3249]. Only whenever the dianion is produced in two steps, namely, by first forming the monoanion by means of sodium or potassium hydride and by then converting the latter with n-butyl lithium into the dianion, are improved yields achieved. The yields even in such case are no higher than somewhat above 80 percent. Beside the desired 4-substituted products, 2-substituted products are also obtained which can be separated only with difficulty.

Whenever acetoacetic acid derivatives are alkylated according to the process of Japanese Patent Publication No. 31,608, first of all the lithium salt must be produced by means of expensive butyl lithium. In that case yields result which lie in the order of magnitude of those which are achieved when working with the dianion.

BROAD DESCRIPTION OF THE INVENTION

An object of the invention is to provide a sample, to find a technically-acceptable process which does not have the disadvantages of the above-described prior art processes. Other objects and advantages of the invention are set out herein or are obvious herefrom to one ordinarily skilled in the art.

The objects and advantages of the invention are achieved by the process of the invention.

The invention involves a process for the production of 4-substituted acetoacetic acid derivatives from the corresponding acetoacetic acid derivatives, characterized in that an acetoacetic acid derivative having the formula

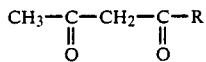

wherein R is alkoxy having 1 to 6C atoms, phenoxy, —NR′$_2$, wherein R′ is alkyl with 1 to 6C atoms or aryl, or NR′$_2$, which is azetidine, pyrrolidine or piperidine, is treated with a secondary amine at an elevated temperature and in the presence of an organic solvent. The water formed is separated. The intermediated is converted into the corresponding 3-enamine carboxylic acid derivative. The derivative is converted by treatment with sodium amide in liquid ammonia into the corresponding sodium salt. The sodium salt is converted by treatment with a halogen compound having the formula $R_1CH_2X$ or $R_1R_2CHX$ wherein $R_1$ and $R_2$ each are alkyl, alkenyl, alkinyl or aryl and X is chlorine, bromine or iodide, into the corresponding 4-substituted enamino derivative. The derivative is hydrolyzed into the 4-substituted acetoacetic acid derivative.

Preferably pyrrolidine or azetidine is used as the secondary amine. Preferably 1 to 1.4 mole of sodium amide is used per mole of acetoacetic acid derivative. Liquid ammonia is also preferably used as solvent during the conversion step with the halogen compound. In one preferred version, after formation of the sodium salt, the liquid ammonia is left in the reaction mixture and an additional organic solvent is used in the continued reaction with the halogen compound. In another preferred version, after the formation of the sodium salt, the liquid ammonia is distilled off and the further reaction with the halogen compound is carried out in the presence of an organic solvent. Preferably any 2-substitution products occurring are selectively hydrolyzed with water and are separated from the 4-substitution products.

DETAILED DESCRIPTION OF THE INVENTION

The process of the invention consists of several steps. The products of the individual steps can be isolated. But it is also possible to conduct the steps without isolation of the pertinent products so as to provide a one step process.

In the first step, the enamino carboxylic acid derivative is formed according to known methods of the enamine production. The secondary amine, for example, can be dimethylamine, diethylamine, piperidine, morpholine, pyrrolidine and azetidine. Pyrrolidine is preferred.

Subsequently the enamino carboxylic acid derivative is converted with sodium amide in liquid ammonia into the sodium salt. At the same time the solvent can be removed or the enamine carboxylic acid derivative can be used to provide the solution. The quantity of sodium amide is selected such that preferably 1.0 to 1.4 mole thereof is used per mole of starting product. The quantity of liquid ammonia used is not critical, however, advantageously 20 to 30 moles of $NH_3$ is used per mole of starting product.

After formation of the sodium salt there are three variations of the remainder of the invention process. One variation involves carrying out the further conversion directly in liquid ammonia. Another variation involves distilling away the amonia and carrying out the further conversion in an organic solvent. But it is also possible to leave the ammonia in the reaction vessel and to additionally use an organic solvent. The solvents used must have a melting point below the reaction temperature and must be unreactive with strong bases. Furthermore, the sodium-organic-compound must be soluble in the solvent. Examples of solvents effective for such purpose are aromatic hydrocarbons, such as, benzene, toluene, xylene, etc., aliphatic hydrocarbons, such as, hexane, pentane, cyclohexane, etc., ethers, such as, diethyl ether, dioxane, tetrahydrofuran, etc., dimethylsulfoxide, dimethylformamide, hexamethyl phosphoric acid triamide, pyridine, substituted pyridines, etc.

The halogen compound has the formula:

R₁CH₂X or R₁R₂CHX.

wherein $R_1$ and $R_2$ are each hydrogen, alkyl, alkenyl, alkinyl or aryl and X is chlorine, bromine or iodine. Examples of the halogen compound are methyl chloride, methyl bromide, methyl iodide, ethyl chloride, ethyl bromide, propyl bromide, allyl chloride, isopropyl bromide, isopropyl iodide, butyl iodide, butyl bromide, propargyl bromide, benzyl chloride and benzyl bromide.

After alkylation, the end product is liberated by hydrolysis, preferably with the help of a mineral acid, such as hydrochloric acid or sulphuric acid. At the same time, the step is effectively conducted in the presence of a solvent which is not miscible with water and which is preferably the solvent used during the alkylation.

If, beside the 4-substitution products, small quantities of 2-substitution products also occur, it is possible to hydrolyze the latter with water selectively into 2-substituted acetoacetic acid derivatives and to easily separate them. Subsequently, the 4-substitution products are hydrolyzed with aqueous acid into the corresponding 4-substituted acetoacetic acid derivatives.

The formation of the sodium salt and the alkylation may be carried out at temperatures of $-60°$ to $+40°$ C. Whenever operating at higher temperatures and/or with gaseous alkylation agents, pressure is used. Gaseous alkylation agents, dissolved in a solvent, can also be used.

By way of summary, the invention involves a process of preparing 4-substituted acetoacetic acid derivatives by the 4-alkylation of acetoacetic acid derivatives with halogen compounds.

As used herein, all parts, percentages, ratios and proportions are on a weight basis unless otherwise stated herein or otherwise indicated herefrom to one ordinarily skilled in the art.

EXAMPLE 1

3-Oxopentanoic Acid Methyl Ester 116 g of acetoacetic acid methyl ester and 75 g of pyrrolidine were boiled in 350 ml of toluene on a water separator until the theoretical quantity of water was separated. The solution was added drop by drop at $-40°$ C. to a suspension of 47 g of sodium amide in 800 ml of liquid ammonia. The ammonia was removed by allowing the temperature of the reaction solution to rise to $-20°$ C., and then, at such temperature, a solution of 114 g of methyl bromide in 500 ml of toluene was added drop by drop. The reaction solution was filtered and the toluene was removed using a rotary evaporator. The residue, after the addition of 700 ml of methylene chloride and 102 g of concentrated hydrochloric acid thereto, was hydrolyzed for 1 hour at ambient temperature. The two phases were separated, the organic phase was dried and the solvent was removed. 120 g of 3-oxopentanoic acid methyl ester (92 percent) was obtained.

EXAMPLE 2

5-Phenyl-3-Oxopentanoic Acid ter.-Butyl Ester

The example was conducted analogously to Example 1. At $-40°$ to $-50°$ C., 133 g of benzylchloride in 500 ml of toluene was added drop by drop. Then the material was hydrolyzed directly by the addition of 200 ml of water and 102 g of concentrated hydrochloric acid at ambient temperature. The phases were separated and the solvent of the organic phase was removed using a rotary evaporator. 236 g of 5-phenyl-3-oxopentanoic acid ter-butyl ester (95 percent) was obtained.

EXAMPLE 3

5-Methyl-3-Oxohexanoic Acid Ethyl Ester 26 g of acetoacetic acid ethyl ester and 15 g of pyrrolidine were boiled in 70 ml of toluene on a water separator until the theoretical quantity of water was separated. The solution was added drop by drop at $-40°$ C. to a suspension of 8.6 g of sodium amide in 300 ml of liquid ammonia. By heating to room temperature, the ammonia was removed. After the reaction solution had been cooled again to 0° C., isopropyl iodide dissolved in 100 ml of toluene was added at the same temperature. The solution was allowed to react for 3 hours at 0° C. The reaction solution was poured into 200 ml of water. The phases were separated and the toluene of the organic phase was removed using a rotary evaporator. Of the residue, 1.2 g of the first runnings was then distilled off at 1.5 torr ($2 \times 10^2$ Pa) and up to a still temperature of 60° C., which contained above all 2-isopropyl acetoacetic acid ethyl ester. The brownish oil remaining behind was dissolved in 70 ml of methylene chloride, and 21 g of concentrated hydrochloric acid was added. The material was hydrolyzed for 1.5 hours at ambient temperature. The two phases were separated. The organic phase was dried, the solvent was removed and the residue was distilled. 28.1 g of 5-methyl-3-oxohexanoic acid ethyl ester (82 percent) was obtained.

EXAMPLE 4

3-Oxopentanoic Acid Ethyl Ester

The example was conducted analogously to Example 1, except that 120 g of methylbromide was introduced at a 40° C.-reaction-mixture temperature through a gas inlet pipe into the reaction mixture. 127 g of 3-oxopentanoic acid ethyl ester 988 percent) was obtained.

EXAMPLES 5 to 16

Examples 5 to 16 were conducted analogously to Example 1. The materials, conditions and results are set out in the following table:

TABLE

| Example | Educt | —NR₂ | R″X | Solvent | Temp. °C. | Product |
|---|---|---|---|---|---|---|
| 5 | acetoacetic acid methyl ester | pyrrolidine | CH₃Br | diethyleneglycol dimethyl ether | −10° | 3-oxopentanoic acid methyl ester |
| 6 | acetoacetic acid methyl ester | " | " | toluene | −10° | 3-oxopentanoic acid methyl ester |
| 7 | acetoacetic methyl ester | " | " | tetrahydrofuran | −10° | 3-oxopentanoic acid methyl ester |
| 8 | acetoacetic acid methyl ester | " | " | diethyl ether | −10° | 3-oxopentanoic acid methyl ester |
| 9 | acetoacetic acid | " | " | pyridine | −10° | 3-oxopentanoic acid |

TABLE-continued

| Example | Educt | —NR$_2$ | R″X | Solvent | Temp. °C. | Product |
|---|---|---|---|---|---|---|
| 10 | acetoacetic acid methyl ester | ″ | ″ | hexane | −10° | 3-oxopentanoic acid methyl ester |
| 11 | acetoacetic acid methyl ester | ″ | ″ | benzene | 10° | 3-oxopentanoic acid methyl ester |
| 12 | acetoacetic acid ethyl ester | ″ | benzyl chloride | toluene | 30° | 5-phenyl-3-oxopentanoic acid ethyl ester |
| 13 | acetoacetic acid ethyl ester | ″ | allyl chloride | diethyl ether | −20° | 3-oxohept-6-enoi acid ethyl ester |
| 14 | acetoacetic acid ethyl ester | ″ | butylbromide | diethyl ether | −20° | 3-oxooctanoic acid ethyl ester |
| 15 | acetoacetic acid ethyl ester | ″ | CH$_3$I | toluene | 0° | 3-oxopentanoic acid ethyl ester |
| 16 | acetoacetic acid piperidine amide | ″ | benzyl chloride | diethyl ether | −30° | 5-phenyl-3-oxopentanoic piperidine amide |

What is claimed is:

1. Process for the production of a 4-substituted acetoacetic acid derivative from a corresponding acetoacetic acid derivative, which comprises: treating an acetoacetic acid derivative having the formula:

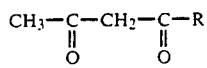

wherein R is an alkoxy having 1 to 6C atoms, phenoxy, —NR′$_2$, wherein R′ is alkyl having 1 to 6C atoms or aryl, or —NR′$_2$, which is azetidine, pyrrolidine or piperidine, with a secondary amine at an elevated temperature and in the presence of an organic solvent, with the water formed being separated, converting the intermediate product of the preceeding step into the corresponding 3-enamine carboxylic acid derivative, converting the 3-enamine carboxylic acid derivative by treatment with sodium amide in liquid ammonia into the corresponding sodium salt, converting the sodium salt by treatment with a halogen compound having the formula R$_1$CH$_2$X or R$_1$R$_2$CHX, wherein R$_1$ and R$_2$ each is alkyl, alkenyl, alkinyl or aryl and X is chlorine, bromine or iodide, into the corresponding 4-substituted enamino derivative, and hydroyzing the 4-substituted enamino derivative into the 4-substituted acetoacetic acid derivative.

2. Process as claimed in claim 1 wherein the secondary amine is pyrrolidine or azetidine.

3. Process as claimed in claim 2 wherein 1 to 1.4 mole of sodium amide is used per mole of acetoacetic acid derivative.

4. Process as claimed in claim 3 wherein liquid ammonia is also used as the solvent during the conversion step using the halogen compound.

5. Process as claimed in claim 3 wherein, after formation of the sodium salt, the liquid ammonia is left in the reaction mixture and an additional organic solvent is used in the continued reaction with the halogen compound.

6. Process as claimed in claim 3 wherein, after the formation of the sodium salt, the liquid ammonia is distilled off and the further reaction with the halogen compound is carried out in the presence of an organic solvent.

7. Process as claimed in claim 3 wherein any 2-substitution products occurring are selectively hydrolyzed with water and are separated from the 4-substitution products.

8. Process as claimed in claim 1 wherein 1 to 1.4 mole of sodium amide is used per mole of acetoacetic acid derivative.

9. Process as claimed in claim 1 wherein liquid ammonia is also used as the solvent during the conversion step using the halogen compound.

10. Process as claimed in claim 1 wherein, after formation of the sodium salt, the liquid ammonia is left in the reaction mixture and an additional organic solvent is used in the continued reaction with the halogen compound.

11. Process as claimed in claim 1 wherein, after the formation of the sodium salt, the liquid ammonia is distilled off and the further reaction with the halogen compound is carried out in the presence of an organic solvent.

12. Process as claimed in claim 1 wherein 2-substitution products occurring are selectively hydrolyzed with water and are separated from the 4-substitution products.

* * * * *